United States Patent [19]

Suzuki et al.

[11] Patent Number: 5,468,905
[45] Date of Patent: Nov. 21, 1995

[54] BICYCLO[4,1,0]HEPTANE-2,4-DION DERIVATIVES, ITS SYNTHETIC INTERMEDIATES AND PROCESS FOR THE MANUFACTURE THEREOF

[75] Inventors: Junji Suzuki, Takaoka; Masami Hatano; Shinichi Imaizumi, both of Odawara, all of Japan

[73] Assignee: Nippon Soda Co., Ltd., Tokyo, Japan

[21] Appl. No.: 117,158

[22] PCT Filed: Jan. 29, 1992

[86] PCT No.: PCT/JP92/00084

§ 371 Date: May 25, 1994

§ 102(e) Date: May 25, 1994

[87] PCT Pub. No.: WO92/13821

PCT Pub. Date: Aug. 20, 1992

[30] Foreign Application Priority Data

Jan. 31, 1991 [JP] Japan .................................. 3-029202

[51] Int. Cl.$^6$ ..................................................... C07C 45/48
[52] U.S. Cl. .......................... 568/346; 568/374; 560/119; 560/124

[58] Field of Search ..................................... 568/346, 347, 568/374; 560/119, 124

[56] References Cited

U.S. PATENT DOCUMENTS

| | | | |
|---|---|---|---|
| 3,932,511 | 1/1976 | Schaafsma et al. | 568/347 |
| 4,399,310 | 8/1983 | Greco | 568/346 |
| 4,414,418 | 11/1983 | Lehky | 568/346 |
| 5,228,898 | 7/1993 | Ueda et al. | 568/376 |

OTHER PUBLICATIONS

Enda et al, J.A.C.S., vol. 107, pp. 5495–5501 (1985).
Kutney et al, Can. J. Chem., vol. 59, pp. 3162–3167 (1981).

*Primary Examiner*—James H. Reamer
*Attorney, Agent, or Firm*—Joseph C. Mason, Jr.; George B. Oujevolk; Louise A. Foutch

[57] ABSTRACT

Compounds represented by general formulas (I) and (II), useful as the intermediates for agricultural chemicals, particularly herbicidal compounds, wherein $R^1$ and $R^2$ represent each hydrogen, alkyl or $COOR^3$:$R^3$ represents alkyl: and $R^4$ represents alkyl.

2 Claims, No Drawings

BICYCLO[4,1,0]HEPTANE-2,4-DION DERIVATIVES, ITS SYNTHETIC INTERMEDIATES AND PROCESS FOR THE MANUFACTURE THEREOF

This application is a 371 of PCT/JP92/00084, filed Jan. 28, 1992.

FIELD OF THE INVENTION

The present invention relates to bicyclo[4,1,0]heptane-2,4-dion derivatives useful as an intermediate, the intermediates for the synthesis thereof and the process for the manufacture thereof.

BACKGROUND ARTS 2-substituted benzoyl-1,3-cyclohexanediones have been known effective as weed killers, and the ones having various subsituents and/or chemical structures have been proposed.

It is an object of the present invention to provide effective compounds as the intermediates for synthesizing herbicidal compounds.

DISCLOSURE OF THE INVENTION

The present invention is directed to a compound represented by the general formula (I):

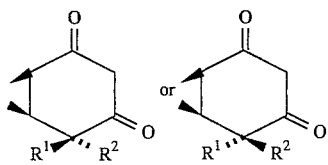

wherein $R^1$, $R^2$ denotes each independently hydrogen, alkyl or —$COOR^3$, and $R^3$ denotes alkyl, and the process for the manufacture thereof, and a compound represented by the general formula (II):

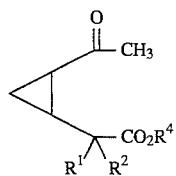

wherein $R^1$, $R^2$ are as defined above and $R^4$ denotes alkyl, and the process for the manufacture thereof.

The compound of the general formula (I) is prepared from the compound of the general formula (II) according to the process shown below;

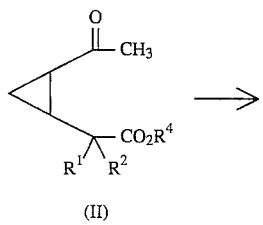

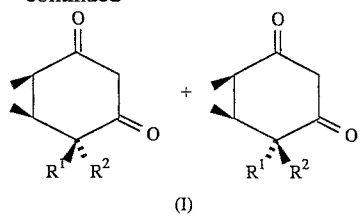

wherein $R^1$, $R^2$ and $R^4$ are as defined above.

The reaction shown above is accomplished by reacting a cyclopropane derivative of the general formula (II) in an adequate solvent and in the presence of a base.

As the solvent described above, alcohols such as methanol and ethanol can be used, and the sodium alcoholate or potassium alcoholate thereof can be used as the base described above.

The reaction can be accomplished at a temperature in a range of from room temperature to 150° C., and preferably at the boiling point of the alcohol used. One to five times amount in mole of the base relatively to the mole of the cyclopropane derivative used, and preferably 1 to 2 times in mole, is used for the reaction.

Them cyclopropane derivatives of the general formula (II) can be manufactured by reacting a ketone of the general formula (III) with an ester of the general formula(IV) in the presence of a base according to the process shown below;

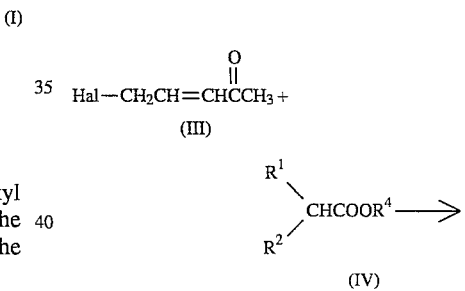

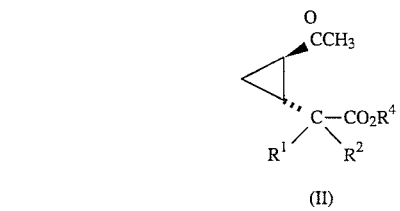

wherein $R^1$, $R^2$ and $R^4$ are as defined above, and Hal denotes halogen.

The foregoing reaction is normally accomplished in an adequate solvent. As the solvent, benzene, toluene and the like can be used besides alcohols, however, it is the most preferable to use alcoholate as a base in alcohol. In the reaction, bicyclic compounds represented by the general formula (I) can be prepared without isolating cyclopropane derivatives of the formula (II) when more than 2 moles of alcoholate is used. The halogen is preferably chlorine.

As shown below, a compound of the general formula (VI) having herbicidal activity can be readily prepared by reacting the bicyclic compound of the general formula (I) with chloride benzoate of the general formula (V).

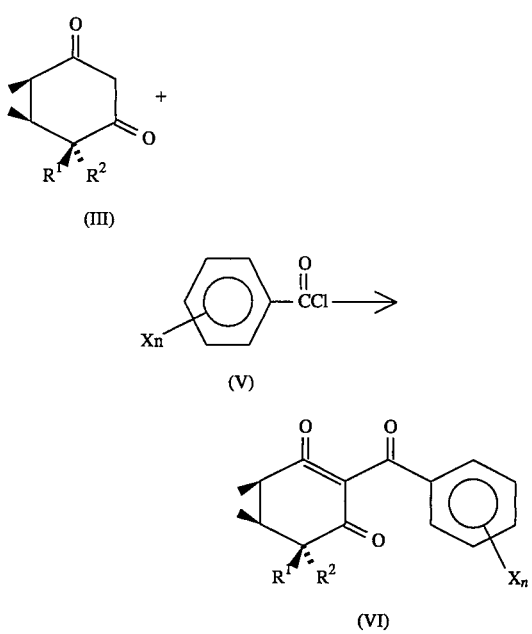

(III)

(V)

(VI)

wherein Xn denotes a substituent.

It is described in the International Publication No. WO 91/00260 Gazette that the compound represented by the general formula (VI) shows herbicidal activity.

The compound specified in this invention may have the tautomers as shown below.

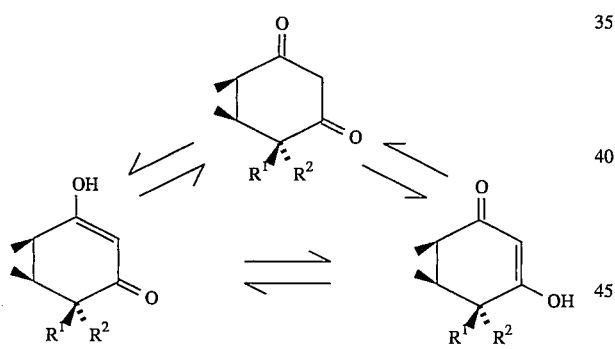

The chemical structures of the compounds according to the invention and other compounds were determined by using IR, NMR, MS and other analytical apparatuses.

BEST MODE FOR CARRYING OUT THE INVENTION

Now, the present invention is practically explained with reference to Examples and Practical Examples.

EXAMPLE 1

(2-acetylcyclopropyl)diethyl methylmalonate

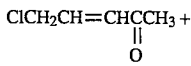

-continued

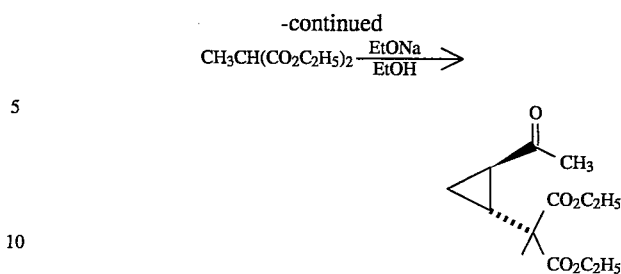

In 25 ml of ethanol was added 5.15 g of powdered sodium ethylate, then dissolved. To the solution, 13.2 g of diethyl methylmalonate was added at room temperature, then 9.5 g of 5-chloro-3-pentane-2-on (90% purity) was further fed dropwise thereto for 30 min. at a temperature of from 0° to 10° C. After reacting the solution for 3 hours at room temperature, ethanol therein was removed by distillation under reduced pressure, then an extraction was made with ethyl acetate after pouring the solution into ice water. The extract was dehydrated with magnesium sulfate, then the solvent therein was removed by distillation, affording 17.3 g of the objective product (98.5% purity) by distillation under reduced pressure. Boiling point of the product was in a range of from 130° to 135° C., and all of the compound obtained were in trans-form.

EXAMPLE 2

Cis- and trans-5-ethoxycarbonyl-5-methylbicyclo[4,1,0]heptane-2,4-dion (Compound No. 3 and 1)

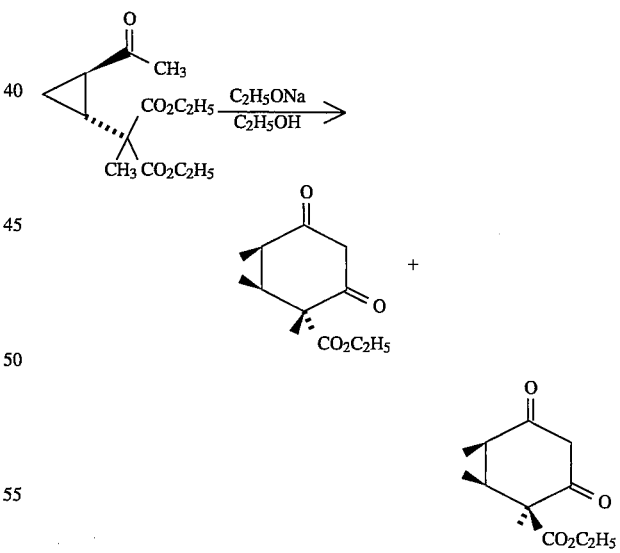

330.7 g of (2-acetylcyclopropyl)diethyl methylmalonate of the formula (II), wherein $R^1$ is $CH_3$, $R^2$ is $CO_2C_2H_5$, and $R^3$ is $C_2H_5$, was added into 975.6 g of 14% sodium ethylate solution in ethanol, then the solution was heated to reflux for 3 hours. After cooling the solution, it was poured into cool aqueous solution of hydrochloric acid, then extracted with ethyl acetate. The extract was then washed with saturated brine. After dehydrating the extract with magnesium sulfate, the solvent was removed by distillation therefrom, affording 87.6 g of the trans form compound of the formula (I), wherein $R^1$ is $CH_3$ and $R^2$ is $CO_2C_2H_5$, in whitish crystals by adding ether into the remained solution.

The solution filtered was further separated by using silica gel chromatography to obtain 8.1 g of the trans-form compound and 27.8 g of the cis-form compound of the formula (I), wherein $R^1$ is $CO_2C_2H_5$ and $R^2$ is $CH_3$.

EXAMPLE 3

Cis- and trans-5-ethoxycarbonyl-5-methylbicyclo[4,1,0] heptane-2,4 -dion (Compound No. 3 and 1)

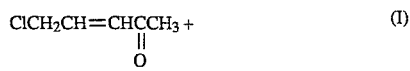 (I)

In 20 ml of ethanol was added 3.52 g of powdered sodium ethylate, then dissolved. To the solution, 4.5 g of diethyl methylmalonate was added at room temperature, then 3 g of 5-chloro-3-pentene-2-on (97.5% purity) was further added thereto at a temperature of from 0° C. to 10° C. After reacting the solution for 1 hours at room temperature, the solution was heated to reflux, for 24 hours. Then the solution was treated according to the procedure in Example 1, affording 1.29 g of the trans-form compound and 0.41 g of the cis-form compound.

The representative examples of the compounds according to the present invention including the compound obtained in the Examples described above are illustrated in Table 1.

TABLE 1

Chemical Structure

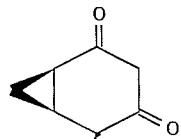

| Compound No. | $R^1$ | $R^2$ | Physical constant [ ] m.p. °C. |
|---|---|---|---|
| 1 | —$CH_3$ | —$CO_2C_2H_5$ | [110–112] |
| 2 | —$CH_3$ | —H | [100–103] |
| 3 | —$CO_2C_2H_5$ | —$CH_3$ | [105–108] |
| 4 | —$CH_3$ | —$CO_2CH_3$ | [122–124] |
| 5 | —$CH_3$ | —$CO_2C_3H_7(i)$ | |

PRACTICAL EXAMPLE

Cis-3-(4-chloro-2-nitrobenzoyl)-5-methylbicyclo [4,1,0]heptane-2,4-dion

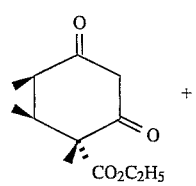 (I)

(1) 5.0 g of trans-5-methyl-5-ethoxycarbonylbicyclo[4,1, 0]heptane- 2,4-dion of the formula (I), wherein $R^1$ is $CH_3$ and $R^2$ is $CO_2C_2H_5$, was dissolved in 50 ml of methylene chloride, then 2.65 g of triethylamine was further added thereto. After cooling the solution to 10° C., 5.24 g of 4-chloro-2-nitrobenzoylchloride was added to the solution and stirred for 2 hours at room temperature. After washing the reacting solution firstly with diluted hydrochloric acid and then water, the solution was dehydrated with magnesium sulfate, and the solvent therein was removed by distillation under reduced pressure. The residues were dissolved into 50 ml of acetonitrile, then added with 0.15 g of potassium cyanide and 2.45 g of triethylamine, and stirred for one night at room temperature. After removing the solvent therein under reduced pressure, methylene chloride was added thereto, then the solution was washed firstly with diluted hydrochloric acid then water, and dehydrated with magnesium sulfate. After removing the solvent in the solution, 9.7 g of trans-3-(4-chloro-2 -nitrobenzoyl)-5-methyl-5-ethoxycarbonylbicyclo[4,1,0] heptane-2,4-dion was obtained.

(2) 73 ml of 1 N NaOH was added to the compound obtained in (1), then the solution was stirred for 24 hours at room temperature. After cooling the solution to a temperature range of from 5° C. to 10° C., 110 ml of ethyl acetate was added thereto, and 48.4 ml of 1 N HCL was further fed dropwise thereto. After stirring the solution for 2 hours, the organic layer was separated and washed with saturated brine, dehydrated with magnesium sulfate, then the solvent therein was removed by distillation under reduced pressure. To the remained solution was added 15 ml of methanol and cooling the solution, affording 4.7 g of the objective product in whitish crystals. The melting point of the product was in a range of from 104° C. to 108° C.

FIELD OF INDUSTRIAL USE

The compounds according to the present invention are useful as the intermediates for the manufacture of agricultural chemicals and the like, and particularly the intermediates for herbicidal compounds.

What we claim is:

1. A compound represented by the formula (I):

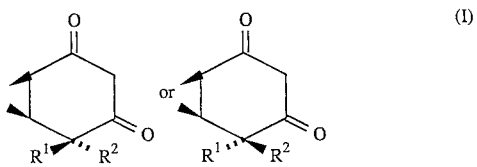

wherein $R^1$ and $R^2$ denote each independently hydrogen, $C_1$–$C_6$ alkyl or —$COOR^3$ and $R^3$ denotes $C_1$–$C_6$ alkyl, with the proviso that both $R^1$ and $R^2$ cannot denote —$COOR^3$.

2. A process for preparing a compound represented by the formula (I):

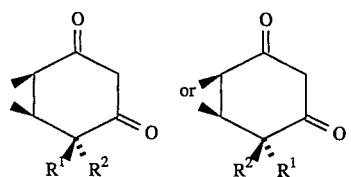 (I)

wherein $R^1$ and $R^2$, denote each independently hydrogen, $C_1$–$C_6$ alkyl or —$COOR^3$ and $R_3$ denotes $C_1$–$C_6$ alkyl with the proviso that both $R^1$ and $R^2$ cannot denote —$COOR^3$ characterized in that the compound is prepared by forming a ring closure in a compound represented by the formula (II):

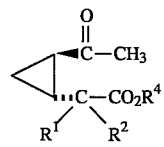 (II)

wherein $R^1$ and $R^2$ are as defined above and $R_4$ denotes $C_1$–$C_6$ alkyl.

* * * * *